(12) United States Patent
Adlerstein et al.

(10) Patent No.: US 12,275,990 B2
(45) Date of Patent: *Apr. 15, 2025

(54) MODIFIED PRIMERS FOR NUCLEIC ACID AMPLIFICATION AND DETECTION

(71) Applicant: Binx Health Limited, Trowbridge (GB)

(72) Inventors: Daniel Adlerstein, Trowbridge (GB); David Pearce, Trowbridge (GB); Anna Dixon, Keynsham (GB); Wellington Fakanya, Trowbridge (GB)

(73) Assignee: Binx Health Limited, Trowbridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/522,434

(22) Filed: Nov. 9, 2021

(65) Prior Publication Data
US 2022/0205031 A1   Jun. 30, 2022

Related U.S. Application Data

(63) Continuation of application No. 14/905,670, filed as application No. PCT/GB2014/052213 on Jul. 18, 2014, now Pat. No. 11,180,798.

(30) Foreign Application Priority Data

Jul. 19, 2013 (GB) .................................... 1312995

(51) Int. Cl.
    C12Q 1/6853   (2018.01)
    C12Q 1/6823   (2018.01)
    C12Q 1/6848   (2018.01)
    C12Q 1/689    (2018.01)

(52) U.S. Cl.
    CPC ......... *C12Q 1/6853* (2013.01); *C12Q 1/6823* (2013.01); *C12Q 1/6848* (2013.01); *C12Q 1/689* (2013.01)

(58) Field of Classification Search
    CPC combination set(s) only.
    See application file for complete search history.

(56) References Cited

U.S. PATENT DOCUMENTS

| 5,418,149 A | 5/1995 | Gelfand et al. |
| 11,180,798 B2 * | 11/2021 | Adlerstein ............ C12Q 1/6853 |
| 2004/0209291 A1 | 10/2004 | Uematsu et al. |

FOREIGN PATENT DOCUMENTS

| WO | WO-9416090 A1 * | 7/1994 | ............ C12N 15/10 |
| WO | WO-9429279 A1 * | 12/1994 | ......... B01J 31/2404 |
| WO | 03/074731 A2 | 9/2003 | |
| WO | 2007/012807 A2 | 2/2007 | |
| WO | WO-2008104791 A1 * | 9/2008 | ........... C12Q 1/6858 |
| WO | 2011/073675 A2 | 6/2011 | |
| WO | 2012/085591 A1 | 6/2012 | |
| WO | 2013/190328 A1 | 12/2013 | |

OTHER PUBLICATIONS

Ono et al., "2'-Fluoro modified nucleic acids: polymerase-directed synthesis, properties and stability to analysis by matrix-assisted laser desorption/ionization mass spectrometry," Nucleic Acids Research, vol. 25, No. 22, pp. 4581-4588. (Year: 1997).*
Compton, 1991, Nucleic acid sequence-based amplification, Nature, 350(6313):91-2.
Longo, 1990, Use of uracil DNA glycosylase t control carry-over contamination in polymersase chain reactions, Gene, 93(1):125-128.
McKinlay, 2011, Genome-Wide Analysis of Nascent Transcription in *Saccharomyces cerevisiae*, G3 (Bethesda), 1(7):549-558.
Notomi, 2000, Loop-mediated isothermal amplification of DNA, Nucleic Acids Research., 28(12):E63.
Suyama, 2007, A proportional analysis method using non-kinetic real-time PCR, J Biotechnol, 128():41-49.
Vincent, 2004, Helicase-dependent isothermal DNA amplification, EMBO Rep., 5(8):795-800.
Walker, 1992, Strand displacement amplification—an isothermal, in vitro DNA amplification technique, Nucleic Acids Res, 20(7):1691-1696.
Wang, 2012, A sensitive fluorescence strategy for telomerase detection in cancer cells based on T7 exonuclease-assisted target recycling amplification, Chem. Comm. 48:5916-5198.
Wiedmann, 1994, Ligase Chain Reaction (LCR)-Overview and Applications, PCR Methods and Applications, 3(4):S51-64.
Wroblewski, 2006, Comparison of Transcription-Mediated Amplification and PCR Assay Results for Various Genital Specimen Types for Detection of Mycoplasma genitalium, J Clin Microbiol, 44(9):3306-3312.

* cited by examiner

*Primary Examiner* — Young J Kim
(74) *Attorney, Agent, or Firm* — Thomas C. Meyers; Sullivan & Worcester LLP (57) ABSTRACT

A method of nucleic acid amplification involving using a first modified primer which provides protection to the amplification product from exonuclease degradation and a second primer. The method provides a double stranded nucleic acid, one strand of which is degraded by a double strand nucleic acid specific exonuclease to form a single stranded nucleic acid, which is protected from exonuclease degradation.

18 Claims, 10 Drawing Sheets

Specification includes a Sequence Listing.

FIG. 8
NG T1 Detection

MODIFIED PRIMERS FOR NUCLEIC ACID AMPLIFICATION AND DETECTION

SEQUENCE LISTING

This application contains a sequence listing filed in electronic form as an ASCII.txt file entitled BINX008-02US-Sequence-Listing.txt, created on Mar. 21, 2022 and having a size of 4 KB. The content of the sequence listing is incorporated herein in its entirety.

TECHNICAL FIELD

The invention relates to methods for detecting the presence of particular nucleic acids in a sample.

BACKGROUND ART

Methods for amplifying nucleic acids are well known in the art.

The detection of amplified nucleic acid products may be carried out in a non-specific way which merely detects the presence of double stranded nucleic acid (for example, by use of a double stranded-DNA intercalating dye such as ethidium bromide or SYBR-green). Alternatively, a semi-specific detection of product may be carried out by resolving approximate molecular weight of the product, for example, by carrying out an electrophoresis of the reaction products prior to detection. Alternatively, there are a number of sequence-specific detection methods which typically involve the hybridization of a sequence-specific nucleic acid probe to the amplified region or which measure the degradation of the probe concomitant with the amplification of the target sequence and make use of the nucleic acid exonuclease activity of the nucleic acid polymerase.

A problem associated with detection of amplified PCR products using sequence-specific probes is due to the fact that PCR produces double stranded amplified products. Therefore in order for a sequence-specific probe to be able to hybridise to the strand of the amplified product to which it is complementary, the strands of the double stranded amplified product must be separated before hybridisation can occur. In order for the sequence specific probe to be capable of displacing the complementary strand of the amplified product, it is possible to increase the concentration of the probe in the detection mixture. However, using high concentrations of probe in the detection mixture increases the noise and as a result decreases the signal to noise ratio.

One way of circumventing the problems associated with the production of a double stranded amplification product is to use the method known in the art as asymmetric nucleic acid amplification, such as asymmetric PCR. Asymmetric PCR involves using unequal primer concentrations, i.e. one of the primers is present in excess, and the other primer of the primer pair is not present in excess. The amplification product therefore comprises predominantly the strand of the amplification product which relates to an extended version of the primer that is present in excess.

However, it is known in the art that asymmetric PCR is less efficient than symmetric or balanced PCR in which the concentration of the forward and reverse primers is equal. This is due to the fact that once the primer that is not present in excess is used up, the primer that is in excess forms a single stranded product with linear rather than exponential reaction kinetics.

An object of the invention is therefore to provide a method for amplifying a nucleic acid which provides an increased signal to noise ratio without compromising the efficiency of the detection method.

DISCLOSURE OF THE INVENTION

Figure 1:
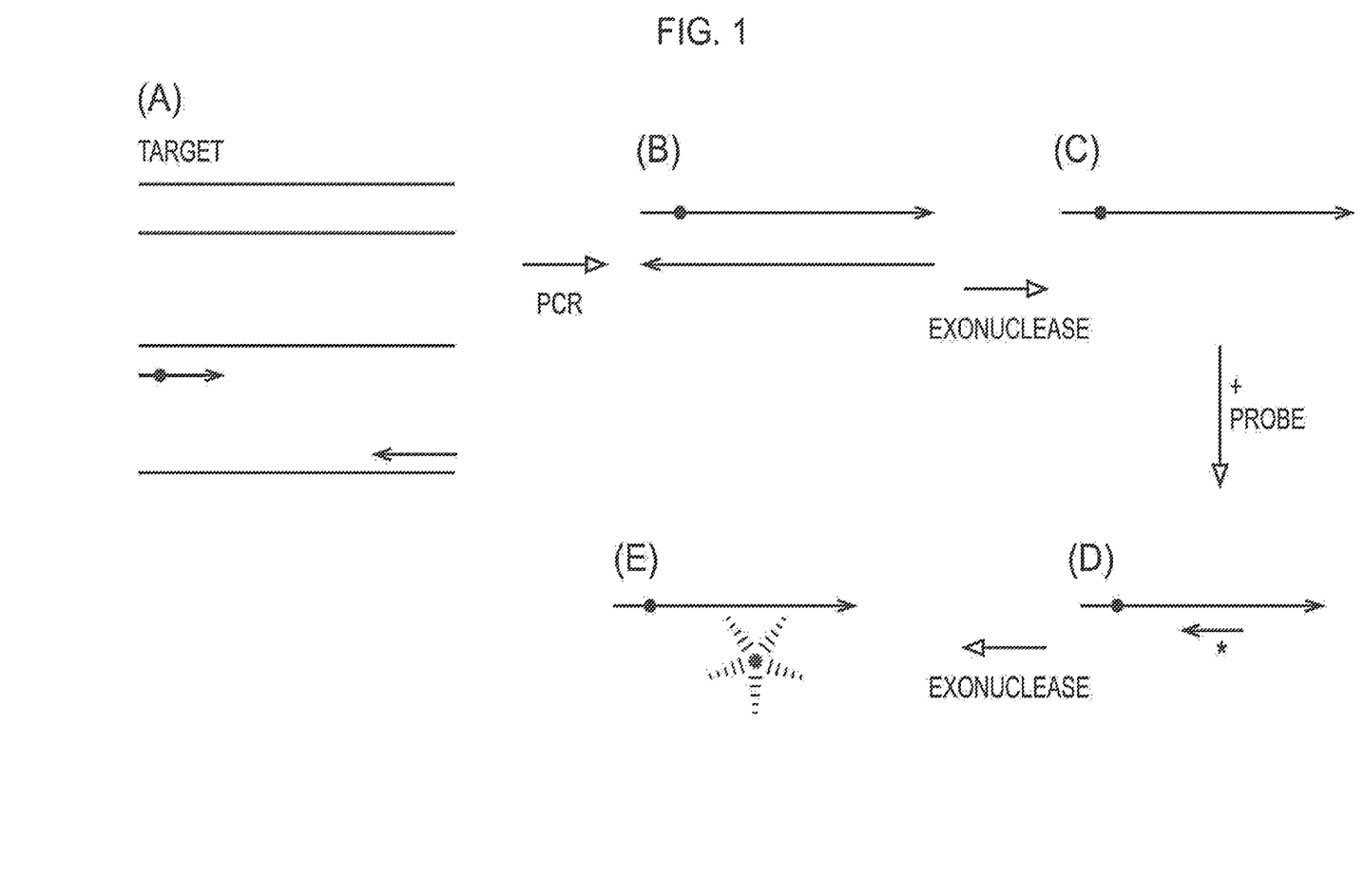
FIG. 1. Overview of the amplification method of the invention.

The inventors have provided a novel amplification method as shown in FIG. 1. In the amplification method, one of the two primers comprises at least one modified nucleotide (see FIG. 1a). Amplification of the target nucleic acid proceeds between the two primers, to provide a double stranded nucleic acid amplification product. The first primer having at least one modified nucleotide (also referred to as "a modified primer") is extended to produce a first strand including the modified nucleotide. The second primer is extended to produce a second strand (see FIG. 1b). A 5' to 3' exonuclease is then provided which is specific for double stranded nucleic acids and which is capable of hydrolysing the second strand but is incapable of hydrolysing the first strand in the region of the at least one modified nucleotide. Therefore the amplified region of the first strand is not hydrolysed by the exonuclease. Therefore a single stranded nucleic acid comprising at least the amplified region of the first strand is provided (see FIG. 1c). This single stranded nucleic acid is protected from exonuclease degradation by virtue of the modified nucleotides included in it.

The single stranded nucleic acid may be detected by performing further steps which provide an increased signal to noise ratio. A labelled probe which specifically hybridises with the single stranded nucleic acid of FIG. 1c is added to the mixture. This probe binds to the single stranded nucleic acid to form a double stranded nucleic acid (see FIG. 1d). The same 5' to 3' exonuclease (although a different one could be used) is then used to hydrolyse the probe. The hydrolysis of the probe releases the label, causing a detectable change to occur to the label which can subsequently be detected (see FIG. 1e). The fact that the exonuclease hydrolyses the probe but not the single stranded nucleic acid (which is protected from exonuclease degradation) allows further probe molecules to hybridise to the single stranded nucleic acid, subsequently providing a detectable change in the signal from the label. Therefore, each single stranded nucleic acid produced can provide multiple signals, thereby increasing the signal to noise ratio compared to using an amplification method using two unmodified primers.

The invention therefore provides a nucleic acid amplification method comprising steps of:
  a) performing nucleic acid amplification on a sample, using a first primer including at least one modified nucleotide ("modified primer") and a second primer, wherein the amplification provides a double stranded nucleic acid comprising a first strand comprising the modified primer and a downstream amplified region; and a second strand; and
  b) incubating the double stranded nucleic acid of a) with a 5' to 3' double stranded nucleic acid specific exonuclease which hydrolyses the second strand but does not hydrolyse the amplified region of the first strand, to provide a single stranded nucleic acid comprising the amplified region of the first strand.

Surprisingly, the inventors have found that the method of the invention is capable of producing a single stranded amplification product, which allows for easy detection. The method of the invention does not suffer from the disadvantages such as inefficiency that are associated with other amplification methods which result in a single stranded nucleic acid product, e.g. asymmetric PCR.

Usually, step a) is performed a number of times (e.g. multiple PCR cycles) before step b) is performed. Thus the hydrolysis of step b) is delayed until significant amplification has occurred, e.g. amplification of at least 1000-fold.

The amplification method may further comprise steps of:
c) incubating the product of b) with a probe including a label, wherein the probe specifically hybridises to the single stranded nucleic acid;
d) incubating the product of c) with a 5' to 3' double stranded nucleic acid specific exonuclease which hydrolyses the probe but does not hydrolyse the amplified region of the first strand, wherein hydrolysis of the probe leads to a detectable change in the signal from the label; and
e) detecting the change.

Surprisingly, the inventors have found that the method of the invention can be used to detect the presence of the single stranded nucleic acid and simultaneously achieve an increased signal to noise ratio. The fact that the exonuclease hydrolyses the probe but not the single stranded nucleic acid allows further probe molecules to hybridise to the single stranded nucleic acid one after another providing an increased signal. Each single stranded nucleic acid that is produced during the amplification step can therefore provide multiple signals and therefore can be detected numerous times. Hydrolysis of the probe can cause the environment of the label to change. The label is no longer attached to the full length probe, and is instead free, or attached to a single nucleotide or short part of the probe. This change in environment of the label leads to a change in the signal from the label. The change in signal from the label can be detected to detect the presence of the nucleic acid of interest.

The invention also provides a kit comprising a modified primer having at least one modified nucleotide; and an exonuclease, wherein the exonuclease is a 5' to 3' double stranded nucleic acid specific exonuclease.

Where dUTP is used in PCR instead of dTTP, uracil is incorporated into the first strand and the second strand during amplification. When a series of amplification reactions are performed, uracyl-N-glycosylase (UNG) may be added prior to amplification to ensure that any carry-over contamination occurring following a previous amplification is removed whilst leaving any sample DNA unaffected (as these contain thymine rather than uracil), reducing the occurrence of false positive results. The inventors have shown that modified primers may be used to produce a single stranded nucleic acid without interfering with activity of UNG prior to amplification.

The invention therefore also provides a nucleic acid amplification method comprising steps of:
i. incubating a sample with uracil-N-glycosylase; and
ii. performing nucleic acid amplification on the product of i. using a first primer including at least one modified nucleotide ("modified primer"), a second primer, and dUTP in the absence of dTTP, wherein the amplification provides a double stranded nucleic acid comprising a first strand comprising the modified primer and a downstream amplified region; and a second strand.

The method may further comprise a step of:
iii. incubating the double stranded nucleic acid of ii. with a 5' to 3' double stranded nucleic acid specific exonuclease which hydrolyses the second strand but does not hydrolyse the amplified region of the first strand, to provide a single stranded nucleic acid comprising the amplified region of the first strand.

The method may further comprise the steps of:
iv. incubating the product of iii. with a probe including a label, wherein the probe specifically hybridises to the single stranded nucleic acid;
v. incubating the product of iv. with a 5' to 3' double stranded nucleic acid specific exonuclease which hydrolyses the probe but does not hydrolyse the amplified region of the first strand, wherein hydrolysis of the probe leads to a detectable change in the signal from the label; and
vi. detecting the change.

The invention also provides a kit comprising a modified primer having at least one modified nucleotide, dUTP and UNG. The kit may also include an exonuclease, wherein the exonuclease is a 5' to 3' double stranded nucleic acid specific exonuclease.

The kits of the invention may be used to perform the methods of the invention.

Nucleic Acid Amplification

Nucleic acid amplification may be performed using any method known in the art, including the polymerase chain reaction (PCR), the ligase chain reaction (LCR)[1], strand displacement amplification (SDA)[2], transcription mediated amplification[3], nucleic acid sequence-based amplification (NASBA)[4], Helicase-dependent amplification[5] and loop-mediated isothermal amplification[6].

A standard amplification mixture for PCR comprises: a first primer and a second primer wherein the two primers are complementary to the 3' ends of each of the sense and antisense strand of the target nucleic acid, a thermostable DNA polymerase, e.g. Taq polymerase isolated from the thermophilic bacterium, *Thermus aquaticus*, deoxynucleoside triphosphates (dNTPs), buffer solution, divalent cations, e.g. magnesium or manganese ions, and monovalent cations, e.g. potassium ions.

Alternative thermostable DNA polymerases are, Pfu polymerase isolated from *Pyrococcus furiosus* which has a proof reading activity absent from Taq polymerase and is therefore a higher fidelity enzyme.

As mentioned above, dUTP may be used instead of dTTPs. Where dUTPs are used, UNG may be added to the sample prior to amplification to remove any carry-over contamination (e.g. that is present in the environment due to leakage from a previous experiment) without affecting the nucleic acids present in the sample.

Uracil-N-glycosylase (UNG) is also abbreviated in the art to UDG. Any UNG may be used in the methods of the invention which is capable of hydrolysing DNA including uracil. For example, the UNG used in the methods and kits of the invention may be human UNG or *E. coli* UNG.

Where a series of amplification reactions are performed using dUTPs, using UNG allows carry-over contamination between separate reactions to be reduced. Any leaked amplified product that becomes present in the sample can be removed using UNG prior to amplification. The nucleic acid amplification of the present invention uses a first primer having at least one modified nucleotide and a second primer. The at least one modified nucleotide is incorporated into the first strand of the double stranded nucleic acid amplification product. As described below the nucleotide modification may be any modification which is not susceptible to hydrolysis by the exonuclease of the invention. The first primer having at least one modified nucleotide may be either the forward primer or the reverse primer. This first strand which includes the modified primer is also the strand to which the probe used in the present invention is capable of specifically hybridising. The second primer is incorporated into the second strand of the double stranded nucleic acid amplification product.

The second primer can be hydrolysed by the exonuclease. As a consequence the second strand which is produced as a result of amplification of the second primer can be hydrolysed by the exonuclease.

The nucleic acid amplification used in the invention may be symmetric nucleic acid amplification, e.g. symmetric PCR, i.e. the forward and reverse primers may be present at substantially the same concentration. Alternatively the nucleic acid amplification used in the invention may be asymmetric nucleic acid amplification e.g. asymmetric PCR, i.e. one of the primers is present in excess, and the other primer is not present in excess. The methods of the invention provide high signal to noise ratio even when symmetric nucleic acid amplification such as symmetric PCR is used in favour of asymmetric nucleic acid amplification such asymmetric PCR.

Amplification Products

The amplification products are the nucleic acids formed from the nucleic acid amplification step of the present invention. The nucleic acid amplification of the invention provides double stranded nucleic acids as amplification products. Preferably the nucleic acid amplification provides predominantly double stranded amplification products. Double stranded nucleic acids as amplification products are generally the result of symmetric nucleic acid amplification such as symmetric PCR. Alternatively, the nucleic acid amplification may provide a lower amount of double stranded amplification products amongst predominantly single stranded nucleic acids as amplification products. Single stranded nucleic acids as amplification products are generally the result of asymmetric nucleic acid amplification such as asymmetric PCR.

Double stranded amplification products that are formed in the nucleic acid amplification step of the present invention comprise a first strand and a second strand. The first strand is formed by extension of the first primer and the second strand is formed by extension of the second primer. The at least one modified nucleotide of the first primer is therefore retained in the first strand. The region downstream of the first primer in the first strand is the downstream amplified region. Due to the presence of the at least one modified nucleotide in the first primer, the downstream amplified region cannot be hydrolysed by the exonuclease.

The second strand preferably does not include any modified nucleotides that cannot be hydrolysed by the exonuclease. The second primer is extended during nucleic acid amplification to form the second strand.

Both the first strand and the second strand may comprise modifications which do not affect the hydrolysis of the strand by the exonucleases used in the present invention.

Modified Nucleotide

The first primer comprises at least one modified nucleotide. A modified nucleotide may be any nucleotide which comprises at least one modified sugar moiety, at least one modified internucleoside linkage and/or at least one modified nucleobase, wherein the modification prevents the nucleotide from being hydrolysed by the exonuclease of the present invention. A modified nucleotide comprises at least one modification compared to naturally occurring RNA or DNA nucleotide.

The at least one modified nucleotide may comprise at least one modified sugar moiety. The modified sugar moiety may be a 2'-O-methyl sugar moiety. The modified sugar moiety may be a 2'-O-methoxyethyl sugar moiety. The modified sugar may be a 2'fluoro modified sugar. As an alternative, the modified sugar moiety may be a bicyclic sugar. Bicyclic sugars include 4'-$(CH_2)n$-O-2' bridges, wherein n is 1 or 2; and 4'-$CH(CH_3)$—O-2' bridges.

The at least one modified nucleotide may comprise at least one modified internucleoside linkage. The at least one modified internucleoside linkage may be at least one phosphoramidite linkage. The at least one modified internucleoside linkage may be at least one phosphorothioate linkage.

The at least one modified nucleotide may comprise at least one modified nucleobase.

The at least one modified nucleotide may comprise more than one modification, e.g. a modified nucleotide may comprise a modified sugar moiety and a modified internucleoside linkage. Alternatively, the modified nucleotide may comprise a modified sugar moiety and a modified nucleobase, or a modified internucleoside linkage and a modified nucleobase. The modified nucleotide may comprise a modified sugar moiety, a modified internucleoside linkage and a modified nucleobase.

The at least one modified nucleotide may be present at any position in the first primer. For example the at least one modified nucleotide may be present at the 5' end of the first primer, or may be present at the 3' end of the first primer, or may be present in the central section of the first primer, or may be interspersed throughout the first primer. Usually, the at least one modified nucleotide is present at the 5' end of the primer. Where a modified nucleotide comprises a modified internucleoside linkage at the 5' end of the primer, the internucleoside linkage between the first and second nucleotide is modified.

The modified primer may comprise multiple modified nucleotides. For example, the modified primer may comprise at least 2, at least 3, at least 4, at least 5, at least 6, at least 7, at least 8, at least 9 or at least 10 modified nucleotides. Specifically, the modified primer may comprise 1, 2, 3, 4, 5, 6, 7, 8, 9, 10, 11, 12, 13, 14, 15, 16, 17, 18, 19, 20, or more than 20 modified nucleotides. Each of the nucleotides of the modified primer may be modified nucleotides.

Where the modified primer comprises multiple modified nucleotides, the modified nucleotides may be contiguous nucleotides in the primer. As an alternative, the modified nucleotides may be spaced out along the primer, i.e. one or more unmodified nucleotides may be present in between the modified nucleotides. The spaces of unmodified nucleotides may comprise, 1, 2, 3, 4, 5, 6, 7, 8, 9 or 10 or more unmodified nucleotides. Preferably, the modified nucleotides are contiguous nucleotides.

Preferably, the first primer comprises 3 or 4 modified nucleotides. Preferably, the first primer comprises 3 or 4 contiguous modified nucleotides. Preferably, the first primer comprises 3 or 4 contiguous modified nucleotides at the 5' end. Preferably, the 3 or 4 modified nucleotides comprise phosphorothioate linkages. In some embodiments, the first primer comprises three contiguous phosphorothioate linkages at the 5' end, i.e. the linkages between the first and second, second and third and third and fourth nucleotides are phosphorothioate linkages. In some embodiments, the first primer comprises four contiguous phosphorothioate linkages at the 5' end, i.e. the linkages between the first and second, second and third, third and fourth and fourth and fifth nucleotides are phosphorothioate linkages.

Primer

As mentioned above, the methods of the invention use a first primer and a second primer. The first primer may be the forward primer and the second primer may be the reverse primer. Alternatively, the second primer may be the forward primer and the first primer may be the reverse primer. The first primer comprises at least one modified nucleotide. The nucleic acid amplification step of the invention causes the modified primer to be extended to form the first strand in the double stranded nucleic acid amplification product. The invention also provides specific modified primers and pairs of primers, as described below.

A primer used in the methods and kits of the invention will generally be at least 10 nucleotides long, e.g. the primer may be 12, 13, 14, 15, 16, 17, 18, 19, 20, 21, 22, 23, 24, 25, 26, 27, 28, 29, or 30 nucleotides in length. The primer can be fully complementary to its target, but in some embodiments (e.g. in TMA) a primer can include a first region which is complementary to its target and a second region which is not. Shorter probe lengths are favoured if the GC content of the probe is high. The length of the first primer includes the at least one modified nucleotide.

In one embodiment, the first primer and the second primer are capable of amplifying a *Chlamydia trachomatis* nucleic acid sequence. The first primer may comprise the nucleotide sequence of

```
                                          (SEQ ID NO: 1)
A*G*A*T*TCCAGAGGCAATGCCAAAGAAA
or

A*G*A*TTCCAGAGGCAATGCCAAAGAAA.
```

N* indicates that the nucleotide at the specified position is a modified nucleotide. Where the modified nucleotide N*comprises a modified internucleoside linkage the modified internucleoside linkage is between the specified nucleotide and the next nucleotide in the 3' direction.

Therefore, the first primer may comprise the nucleotide sequence of SEQ ID NO: 1, wherein nucleotides 1-3 or 1-4 are modified nucleotides. The nucleotides of the primer are numbered from the 5' end. Therefore nucleotides 1-3 or 1-4 are the 3 or 4 nucleotides at the 5' end of the primer. The modified nucleotides may comprise phosphorothioate linkages.

As an alternative, the first primer may comprise the nucleotide sequence of G*T*T*T*GGACACTAGTCAG-CATCAAGCTAGG or G*T*T*TGGACACTAGTCAG-CATCAAGCTAGG, i.e. the first primer may comprise the nucleotide sequence of SEQ ID NO: 2, wherein nucleotides 1-3 or 1-4 are modified nucleotides. The modified nucleotides may comprise phosphorothioate linkages. The invention also provides pairs of primers comprising a first primer comprising SEQ ID NO: 1, wherein nucleotides 1-3 or 1-4 are modified nucleotides optionally comprising phosphorothioate linkages, and a second primer comprising SEQ ID NO: 2, wherein SEQ ID NO: 2 is unmodified, i.e. comprises no modified nucleotides.

The invention also provides pairs of primers comprising a first primer comprising SEQ ID NO: 2, wherein nucleotides 1-3 or 1-4 are modified nucleotides optionally comprising phosphorothioate linkages, and a second primer comprising SEQ ID NO: 1, wherein SEQ ID NO: 1 is unmodified, i.e. comprises no modified nucleotides.

Sample

The sample is a composition on which the method of the invention is performed in order to determine whether a nucleic acid of interest is present. The sample may be a composition in which the nucleic acid to be detected is suspected to be present, or may be a composition in which the nucleic acid to be detected is potentially present. The nucleic acid of interest is capable of being amplified by the first primer and the second primer.

The sample may be material obtained from an animal or plant. The sample may be a cellular sample. The sample may be obtained with minimal invasiveness or non-invasively, e.g., the sample may be obtained from an animal using a swab, or may be a bodily fluid. As an alternative, the sample may be material obtained from food or water. One skilled in the art will appreciate that samples can be diluted prior to the analysis of levels of compounds. Preferably, the sample is obtained from a genital swab, e.g. a vaginal swab.

The sample may have been treated since being obtained from the subject. For example, one skilled in the art will appreciate that samples can be purified, e.g. to purify nucleic acids, diluted, concentrated, centrifuged, frozen, etc. prior to target detection.

An animal may be a vertebrate or non-vertebrate animal. Vertebrate animals may be mammals. Vertebrate mammals may be human. Examples of mammals include but are not limited to mouse, rat, pig, dog, cat, rabbit, primate or the like. The subject may be a primate. Preferably the subject is human.

Nucleic Acid of Interest

The nucleic acid of interest is the nucleic acid which the method of the invention intends to detect the presence or absence of. The nucleic acid of interest comprises the amplicon that is amplified by the nucleic acid amplification. The primers used in the nucleic acid amplification reaction hybridise to the nucleic acid of interest.

The nucleic acid of interest may be a nucleic acid that is specific to a particular pathogen, e.g. to a virus, a bacterium or a fungus. The nucleic acid may therefore be detected in a sample from an animal in order to diagnose a particular disease in an animal.

The nucleic acid may be specific to one of the following pathogens: *Trichomonas vaginalis, Neisseria gonhorroeae, Chlamydia trachomatis, Mycoplasma genitalium* or methicillin resistant *Staphylococcus aureus*.

As an alternative, the nucleic acid may be a sequence endogenous to the subject from which the sample is obtained. The nucleic acid may be a marker for a particular characteristic or a particular predisposition. In this situation, the method of the invention may detect the predisposition of a subject from which a sample is taken to developing a particular disease. As a further alternative, the method of the invention may be used to determine the presence or absence of a particular polymorphism in a subject, e.g. in comparison to another subject, in order to determine similarities and differences between subjects.

Exonuclease

The exonuclease used in the present invention is capable of hydrolysing the second strand of the double stranded nucleic acid amplification product. The exonuclease is not capable of hydrolysing the amplified region of the first strand of the double stranded amplification product. The exonuclease may be capable of hydrolysing part of the first strand, e.g. the 5' end of the first primer if the at least one modified nucleotide is not located at the 5'terminal nucleotide. In embodiments where a probe is present, an exonuclease may be capable of hydrolysing the probe.

The exonuclease of the invention is a 5' to 3' double stranded nucleic acid specific exonuclease. Double stranded nucleic acid specific exonucleases are used such that one strand of the double stranded nucleic acids that are produced as amplification products of the nucleic acid amplification is broken down by hydrolysis from the 5' end to the 3' end by an exonuclease. Where a probe is used, an exonuclease may also be used to break down the probe by hydrolysis from one end following its hybridisation to the first strand. In this step, the exonuclease performs the function of causing a detectable change in the label following hydrolysis of the probe, e.g. by changing the environment in which it is in, in such a way that may be detected in order to determine the presence or absence of the nucleic acid of interest.

Preferably, the exonuclease that is used to hydrolyse the probe is the same as the exonuclease used to hydrolyse the second strand.

The exonuclease may be any 5' to 3' double strand specific exonuclease. The exonuclease may be selected from the group consisting of a *Thermus aquaticus* 5' to 3' exonuclease, a T7 exonuclease, a lambda exonuclease, exonuclease V and a T5 exonuclease. Preferably, the exonuclease is a T7 exonuclease.

Probe

The probe is capable of specifically hybridising to the first strand. The probe may hybridise to the entire length or a portion of the first strand. The probe includes a label. Hydrolysis of the probe leads to a detectable change in the signal from the label. The detection of the change allows for measurement of the presence or absence of the nucleic acid of interest. The entire probe may be capable of specifically hybridising to the first strand. As an alternative, the probe may include a nucleic acid that is capable of specifically hybridising to the first strand.

Probes used in the invention are typically 15 to 45 nucleotides in length, i.e. the probe may be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 nucleotides in length.

The probe can be fully complementary to its target, but in some embodiments the probe can include a first region which is complementary to its target and a second region which is not.

The probe may include one or more additional moieties other than the region capable of hybridising to the target sequence. The additional moieties may be additional nucleic acid sequences or be non-nucleic acid moieties. For example, the probe may include a linker region which attaches it to an array. The additional moiety may be a label moiety. Particular types of labels that may be used are described in more detail below.

Label

The probe and/or primers described above may be linked to a label to assist their detection. The label may be any label which provides a signal. The label may be radioactive, enzymatically active, fluorescently active, luminescently active, or electrochemically active. Hydrolysis of the probe leads to a detectable change in the signal from the probe. This change in the signal from the label may be due to a change in the environment of the label following hydrolysis of the probe.

Where detection of multiple nucleic acid sequences are undertaken simultaneously, for example where two nucleic acids of interest are amplified and detected simultaneously or where detection of a nucleic acid of interest and detection of an internal control nucleic acid sequence are both undertaken simultaneously, the labels used to assist in the detection of the multiple nucleic acid sequences are preferably distinguishable from each other, for example, they may be different fluorophores or they may be different electrochemically active agents or electrochemically active labels providing electrochemically distinguishable activity. As an alternative, the labels may be the same and the detection of the separate nucleic acids may be undertaken in separate detection chambers.

The present invention is especially suitable for use with electrochemically labelled probes and/or primers. In particular, the electrochemical label may include those comprising metallo-carbocyclic pi complexes, that is organic complexes with partially or fully delocalized pi electrons. Suitable labels include those comprising sandwich compounds in which two carbocyclic rings are parallel, and also bent sandwiches (angular compounds) and monocyclopentadienyls. Preferably, the electrochemically active markers are metallocene labels. More preferably they are ferrocene labels. Where the label is an electrochemical label, the detectable change in the signal from the label may be a change in the current which flows through the label on application of potential difference across the label. The label may be a ferrocene label. Examples of labels which may be used in the methods of the invention can be found in WO03/074731, WO2012/085591 and WO 2013/190328. The label may be a fluorescent label. For example, the ferrocene label may have the structure of formula I in WO2012/085591. As an alternative, the ferrocene label may have the structure of formula I in WO 2013/190328.

General

The term "comprising" encompasses "including" as well as "consisting" e.g. a composition "comprising" X may consist exclusively of X or may include something additional e.g. X+Y.

The term "specifically hybridises" has its customary meaning of capable of hybridising to the sequence of the intended target and not to sequences that are not present in the intended target.

Unless specifically stated otherwise, a process comprising a step of mixing two or more components, or incubating two or more components together does not require any specific order of mixing. Thus components can be mixed in any order. Where there are three components then two components can be combined with each other, and then the combination may be combined with the third component, etc.

Unless specifically stated otherwise, the steps of the methods of the invention may be performed in any order.

MODES FOR CARRYING OUT THE INVENTION

Comparison of Standard Primers and Modified Primers in *C. trachomatis* Assay

Figure 2:
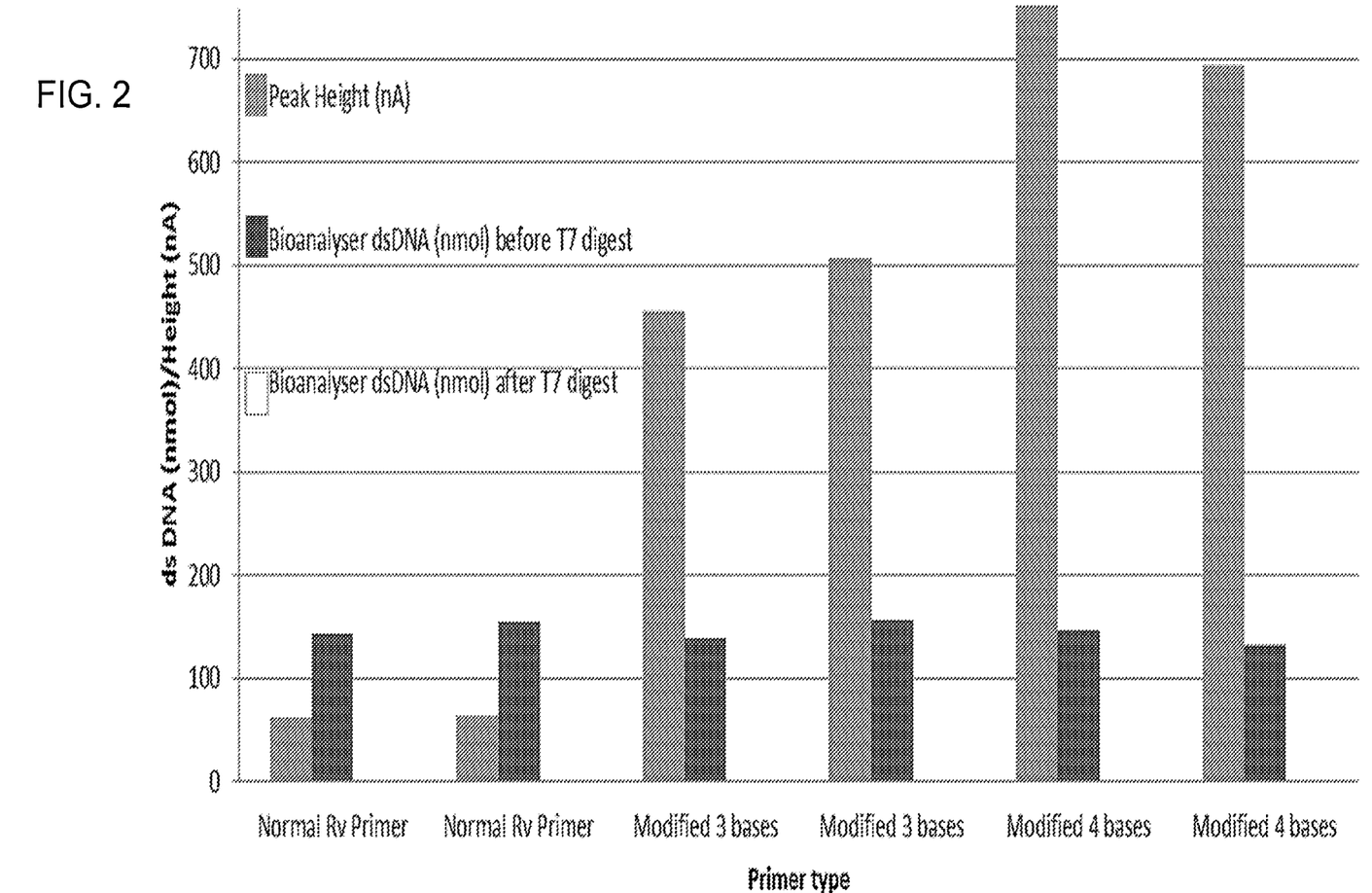
FIG. 2. Comparison of two *C. trachomatis* samples each amplified with standard and modified reverse primer (3 and 4 modified bases).

Reverse (Rv) primers with 3 and 4 consecutive phosphorothioate modifications at the 5' end were tested in several experiments together with an unmodified forward (Fw) primer and compared to peak heights obtained when using normal Rv and Fw primers together. Results are provided in FIG. 2. In the *C. trachomatis* assay, an electrochemically labelled probe hybridises to the strand extended from the reverse primer. Therefore, the reverse primer, rather than the forward primer is modified to prevent degradation, i.e. the first primer is the reverse primer and the second primer is the forward primer.

A substantial increase in electrochemical signal was observed when the modified Rv primers were used compared with standard Rv primers. Four modifications provided a larger increase in peak height than three modifications. This increase was observed across a number of experiments using a range of template concentrations and amplification protocols. Experiments were also carried out to verify the system of primer protection against nuclease degradation including the use of a modified Fw primer.

This is due to the fact that a single-stranded product is produced which is more amenable to probe hybridisation and therefore detection. Furthermore, the assay provides an increased signal by hydrolysing the probe after it hybridises to the first strand, but not allowing the first strand to be hydrolysed because it is protected by the modified nucleotides. In this way, multiple probe molecules are able to hybridise to a single copy of the first strand providing an increased signal.

Compatibility of the Modified Rv Primer with Rapid Amplification

Figure 3:
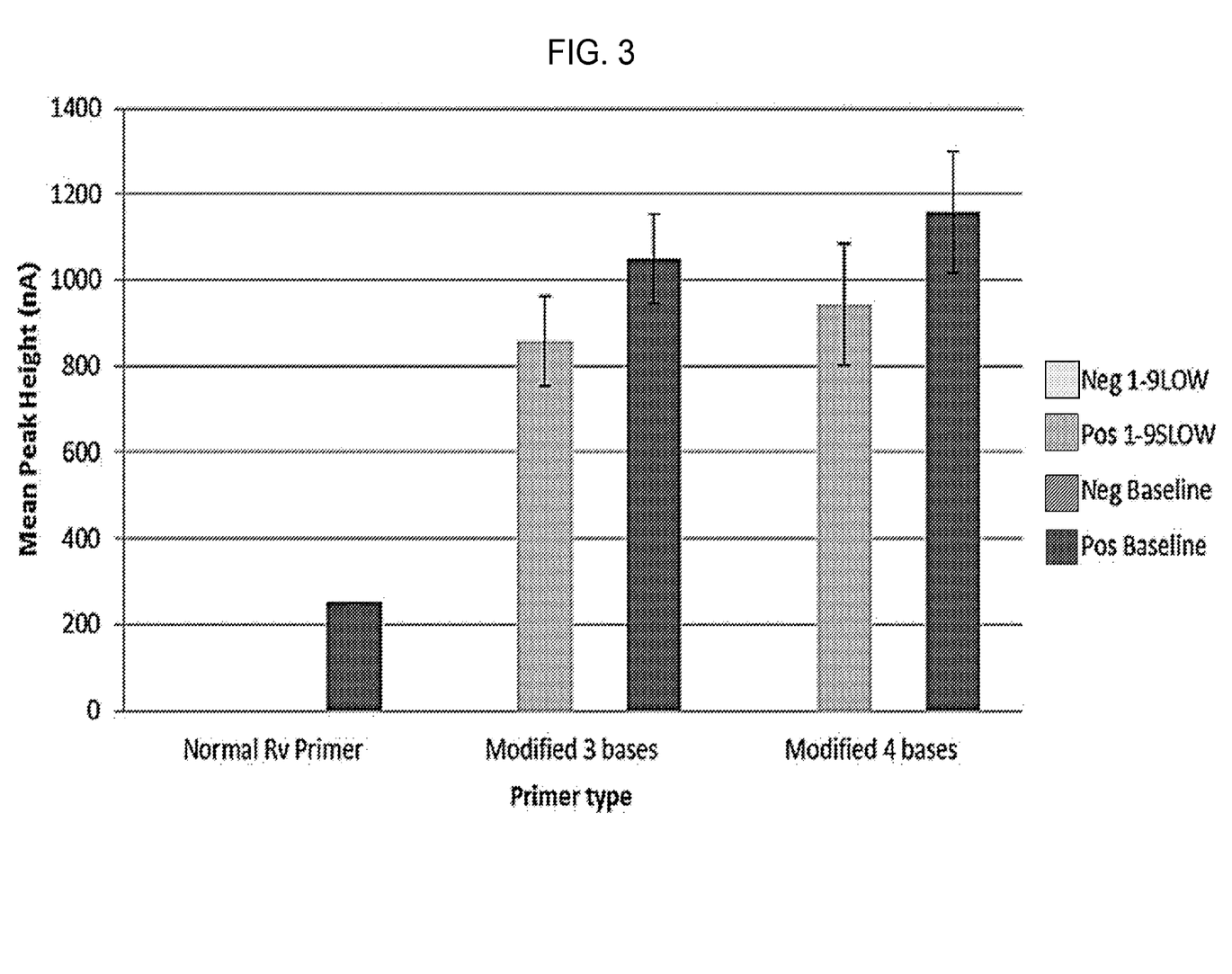
FIG. 3. Amplification and detection of *C. trachomatis* target sequence using standard, 3-base modified and 4-base modified reverse primers using semi-rapid and rapid PCR protocols. Error bars are +/−1 standard deviation from the mean.

Unmodified Rv primers and 3-base modified and 4-base modified Rv primers were used in amplification reactions with unmodified Fw primers. The PCR amplifications were performed using either a semi-rapid protocol (Baseline) or a rapid protocol (1-9 SLOW) in order to determine whether the modified primers could be used in the semi-rapid PCR protocol. The results of these experiments are provided in FIG. 3. All three primer sets had undetectable peak heights in the negative controls. Substantial increases in peak heights relative to the unmodified control were obtained for both amplification protocols (semi-rapid and rapid), with the Rv primer containing four modifications providing increased peak heights compared to three modifications. Therefore, modified primers were found to be compatible with rapid PCR.

Effect of the Modified Rv Primer on the *C. trachomatis* Assay Inclusivity and Exclusivity.

Figure 4:
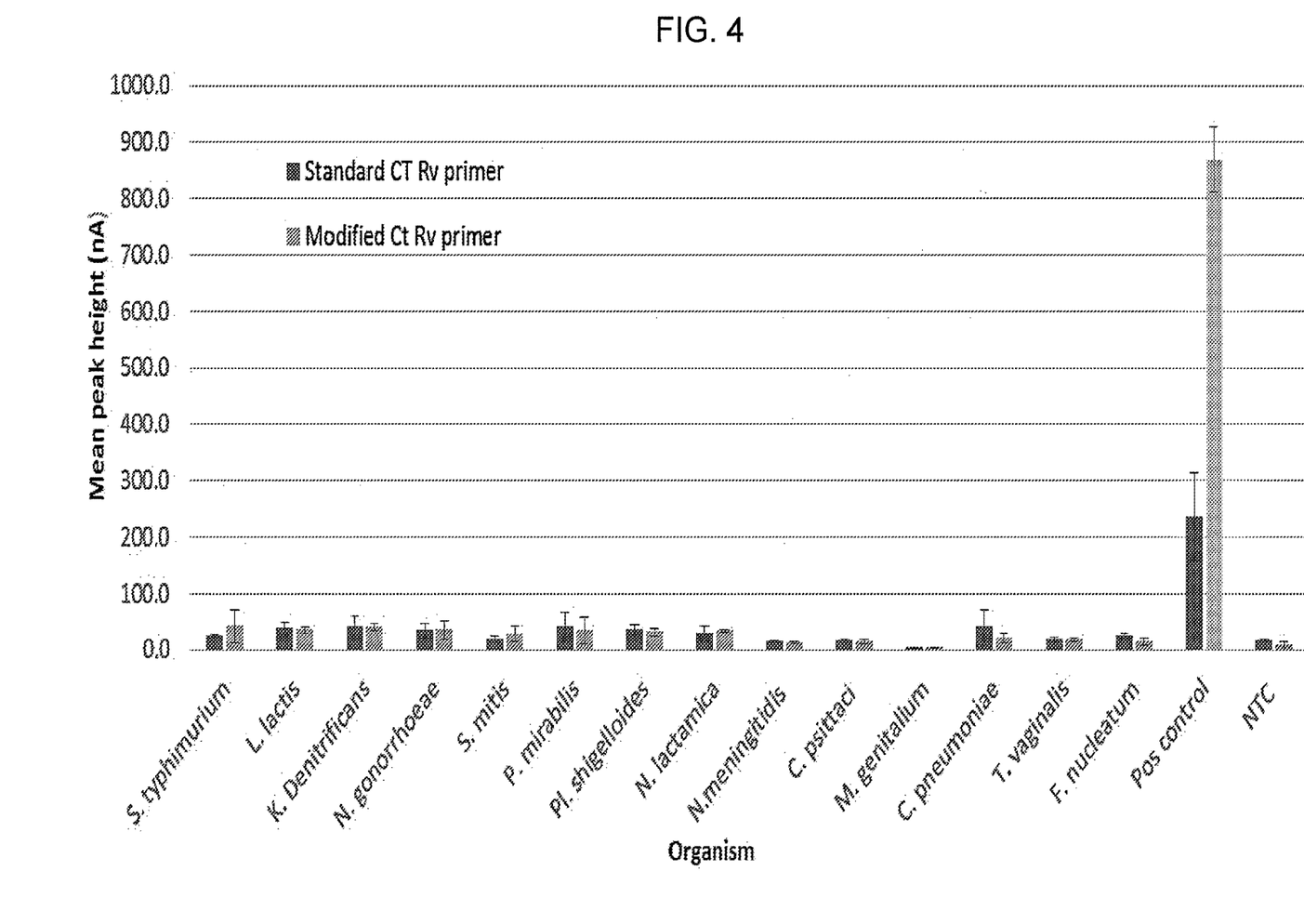
FIG. 4. Exclusivity data for standard and 4-base modified reverse primer with 14 organisms using semi-rapid PCR of *C. trachomatis* target sequence. Error bars are +/−1 standard deviation from the mean.
Figure 5:
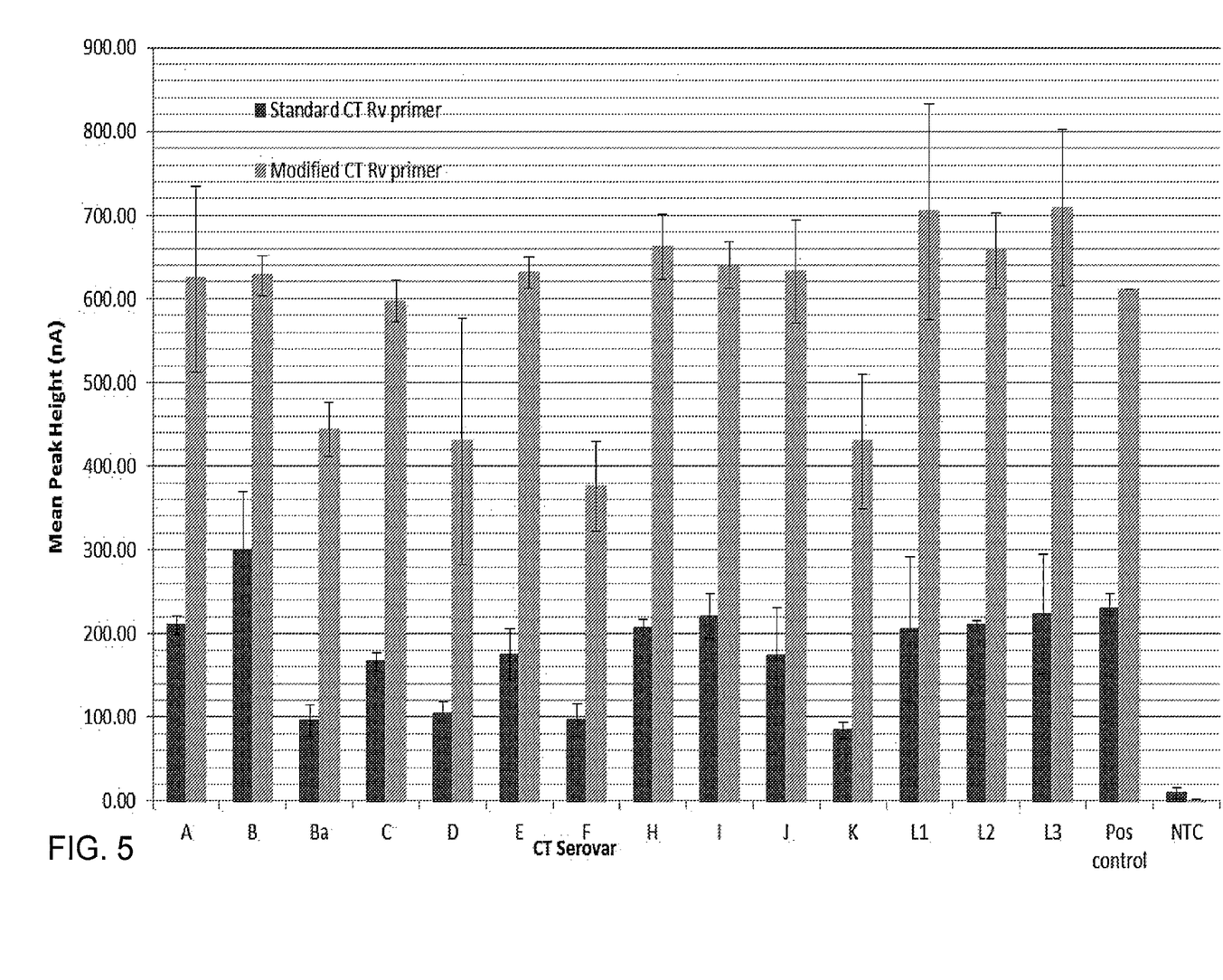
FIG. 5. Inclusivity data using standard and 4-base modified reverse primers with 14 serovars using semi-rapid PCR of *C. trachomatis* target sequence. Error bars are +/−1 standard deviation from the mean.
Figure 6:
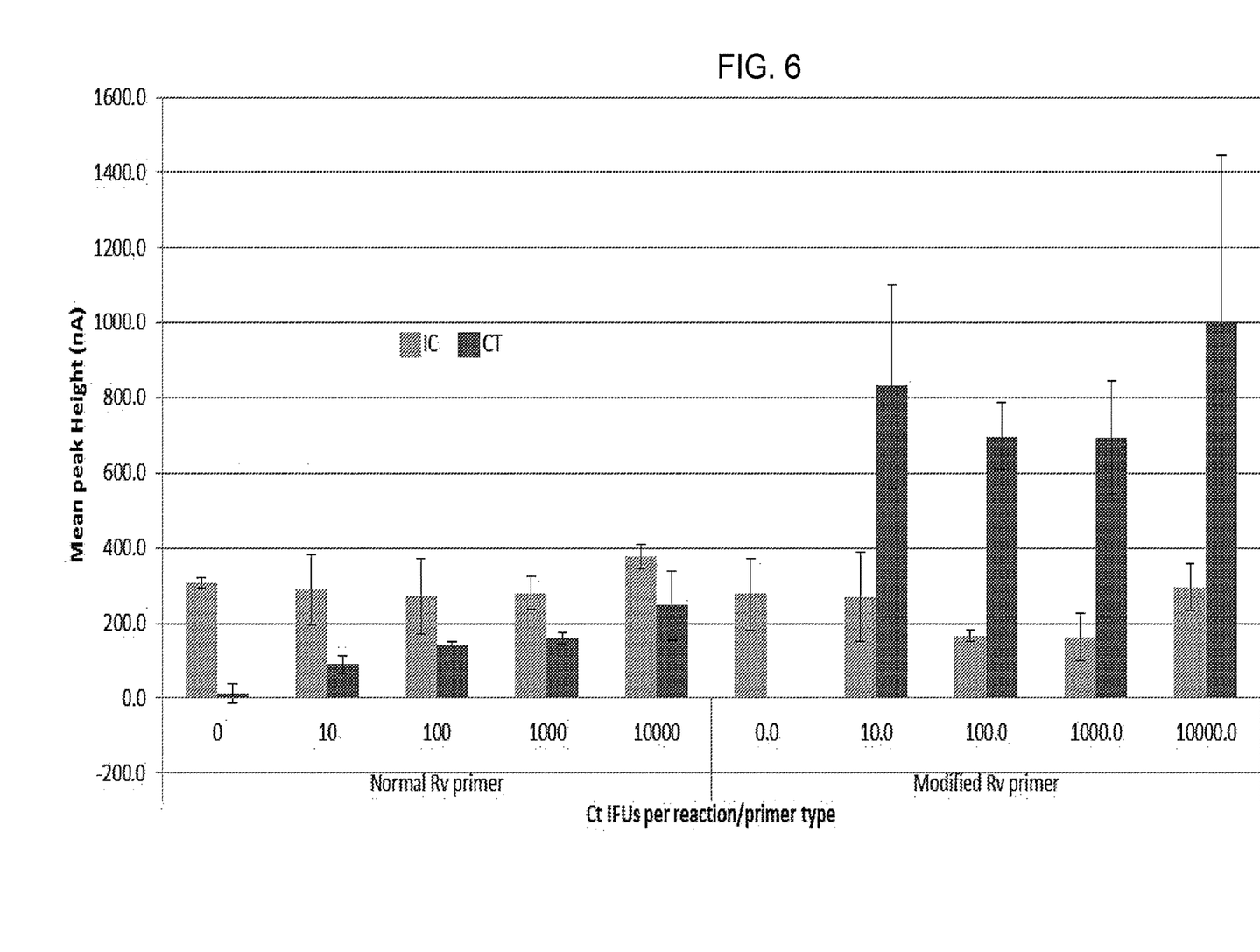
FIG. 6. Comparison of standard and 4-base modified reverse primers using a range of *C. trachomatis* template concentrations and a consistent concentration of internal control nucleic acid. Error bars are +/−1 standard deviation from the mean.

It is known in the art that it is possible for phosphorothioate modifications to affect a primer's annealing properties. Therefore an experiment was carried out to assess any potential effects of using a phosphorothioate-modified Rv primer on the *C. trachomatis* assay inclusivity and exclusivity. A number of organisms were selected to contain species that were clinically relevant, closely related to *C. trachomatis* and those that produced the highest signal outliers in previous exclusivity experiments (using standard primers). This panel was tested using both the standard unmodified Rv primer and the 4 base modified Rv primer using semi-rapid amplification. The results of these experiments are provided in FIG. 4. To establish inclusivity, 14 serovars of *C. trachomatis* were amplified using semi-rapid amplification in the presence of the standard *C. trachomatis* Rv primer or the 4-base modified Rv primer. The amplification products were detected electrochemically using electrochemically labelled probes. The results of these experiments are provided in FIG. 6. The data show that using Rv primers with 4 modified bases at the 5' end does not affect the exclusivity or the inclusivity of the assay.

Effect of the Modified Rv on Degradation of Carry-Over Amplicon by UNG

UNG (Uracyl-N-Glycosylase) together with dUTPs may be used in the *C. trachomatis* assay to prevent false negative results from carry-over contamination by amplicon. It was tested whether use of modified primers would affect the mechanism or ability of UNG to degrade carry-over contamination.

Amplification using standard and 4 base modified *C. trachomatis* Rv primer was carried out to generate test amplicon using dNTPs with dUTP instead of dTTP. Following this, a dilution of each amplicon was used in two subsequent PCRs (using standard Rv or a 4 base modified primer) in the presence or absence of UNG. Following amplification, amplification products were electrochemically detected.

The results demonstrate that whilst using the modified Rv primer produces a greater electrochemical signal (as demonstrated above), amplification products containing the modified Rv primer are susceptible to UNG degradation in the same way that amplification products produced using the standard primer is. Therefore, using a *C. trachomatis* Rv primer with 4 phosphorothioate nucleosides at the 5' end does not affect the ability of UNG to degrade carry-over contamination.

Compatibility of the Modified Rv with the Internal Control

The *C. trachomatis* assay uses an internal control which monitors the assay at each stage and verifies a negative result. Experiments were performed to test whether the use of a modified Rv primer adversely affected the amplification or detection of the internal control.

Figure 7:
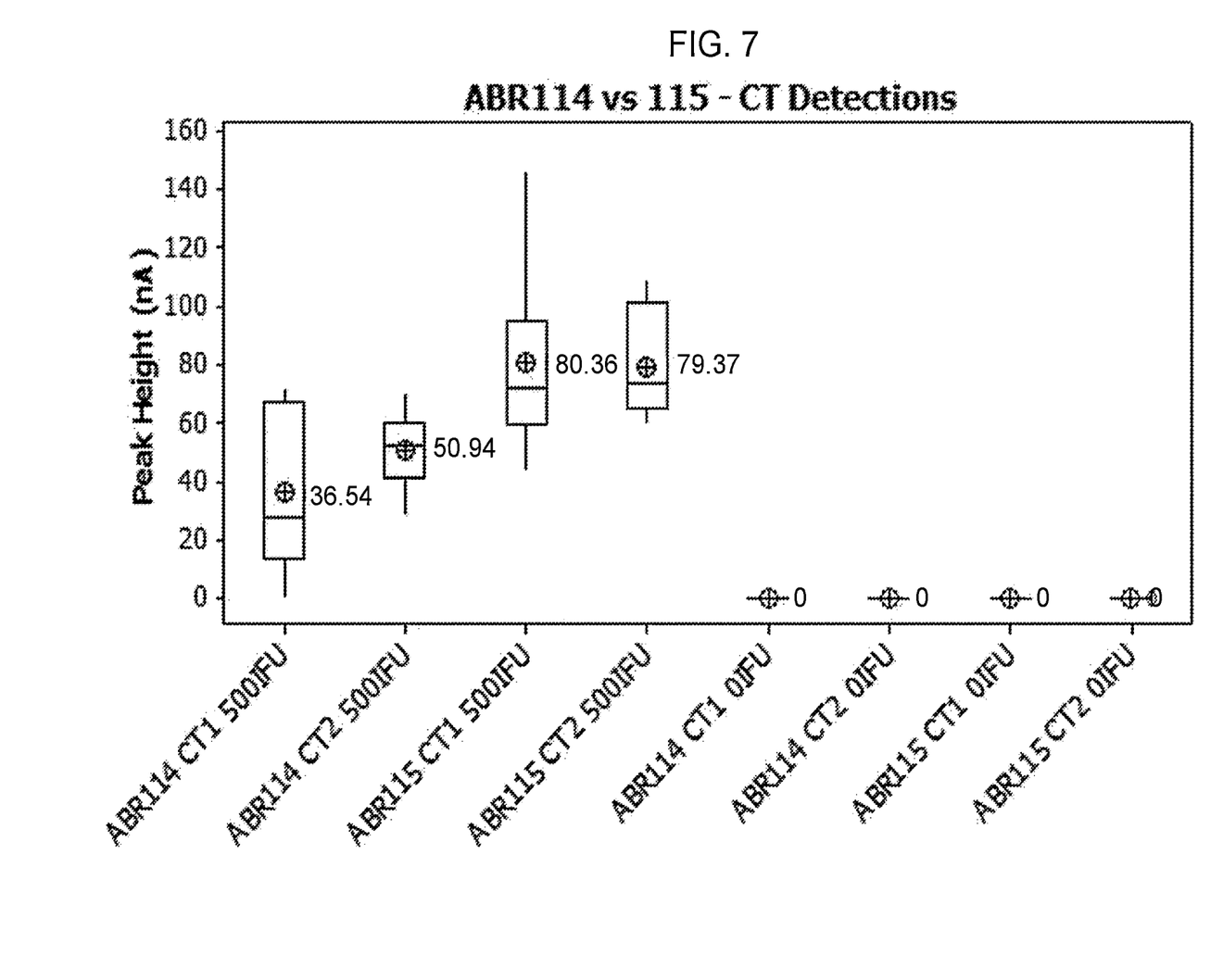
FIG. 7. Boxplot of *C. trachomatis* peak heights obtained with standard (ABR114) and 4-base modified (ABR115) reverse primers (n=10 for all detections) for outer chamber (CT1) and inner chamber (CT2) of a cartridge.
Figure 8:
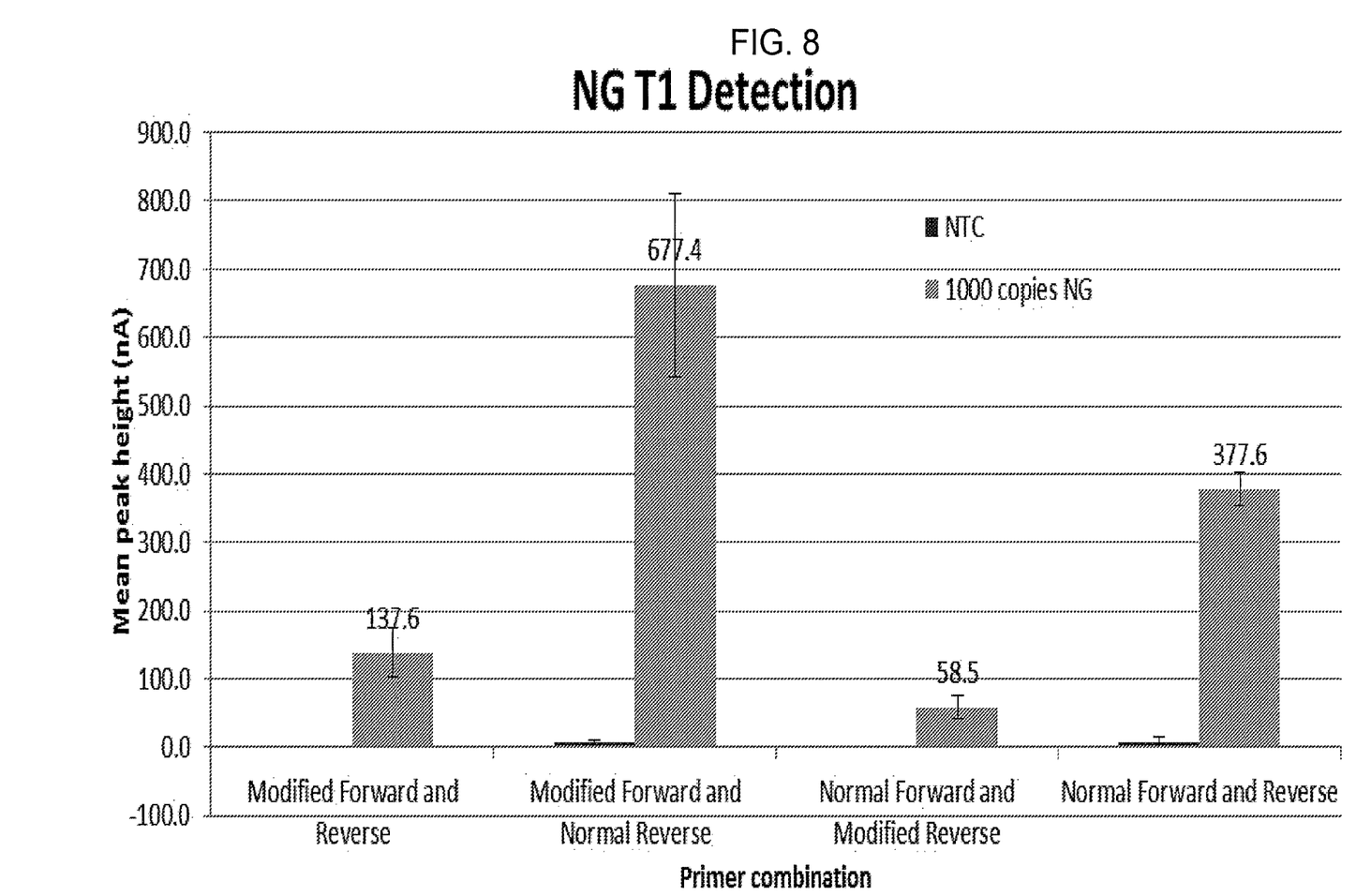
FIG. 8. Amplification and detection of *N. gonhorroeae* target sequence using standard and 4-base modified forward and reverse primers using semi-rapid PCR.
Figure 9:
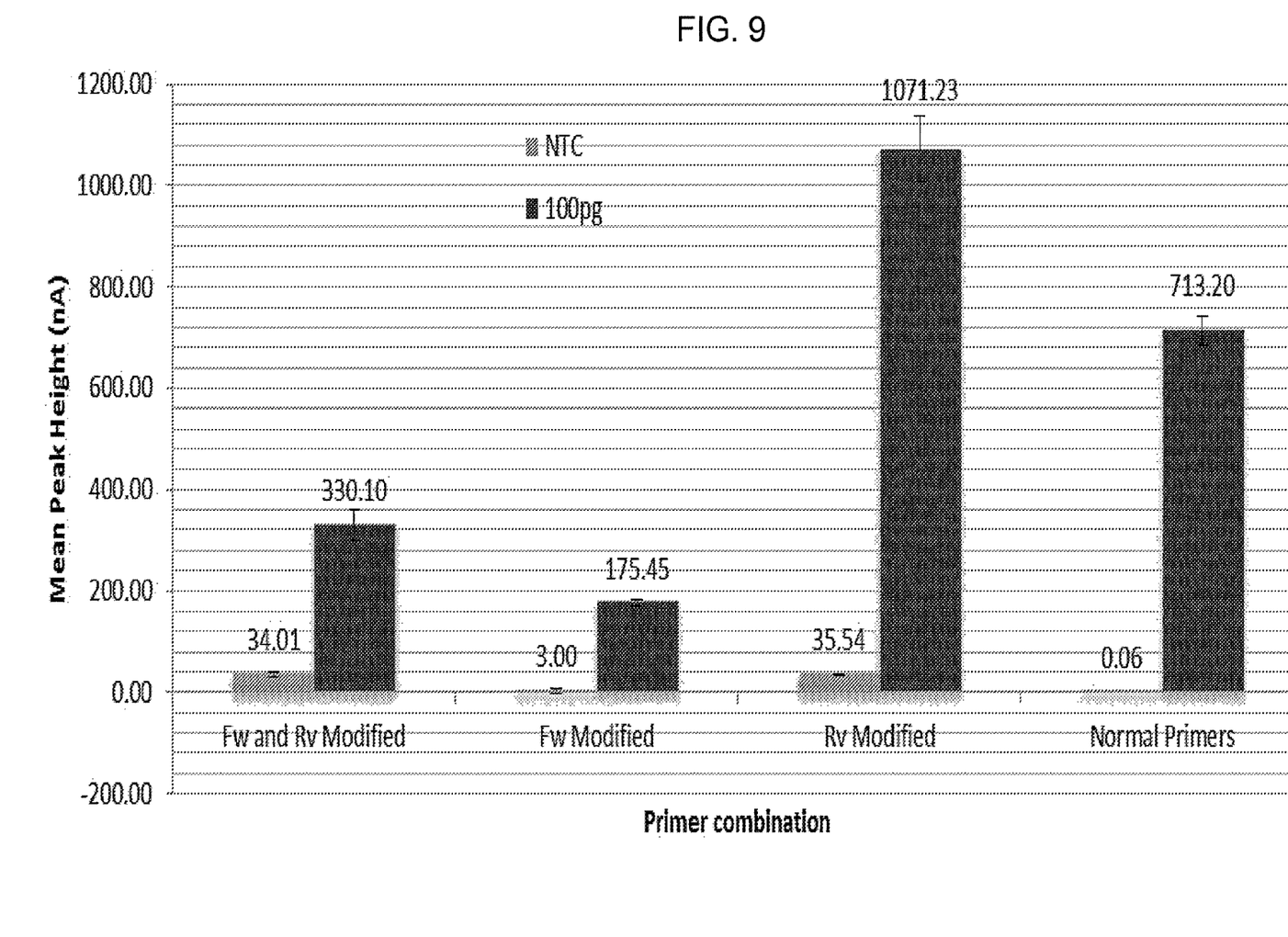
FIG. 9. Amplification and detection of internal control nucleic acid using standard and 4-base modified forward and reverse primers using semi-rapid PCR.
Figure 10:
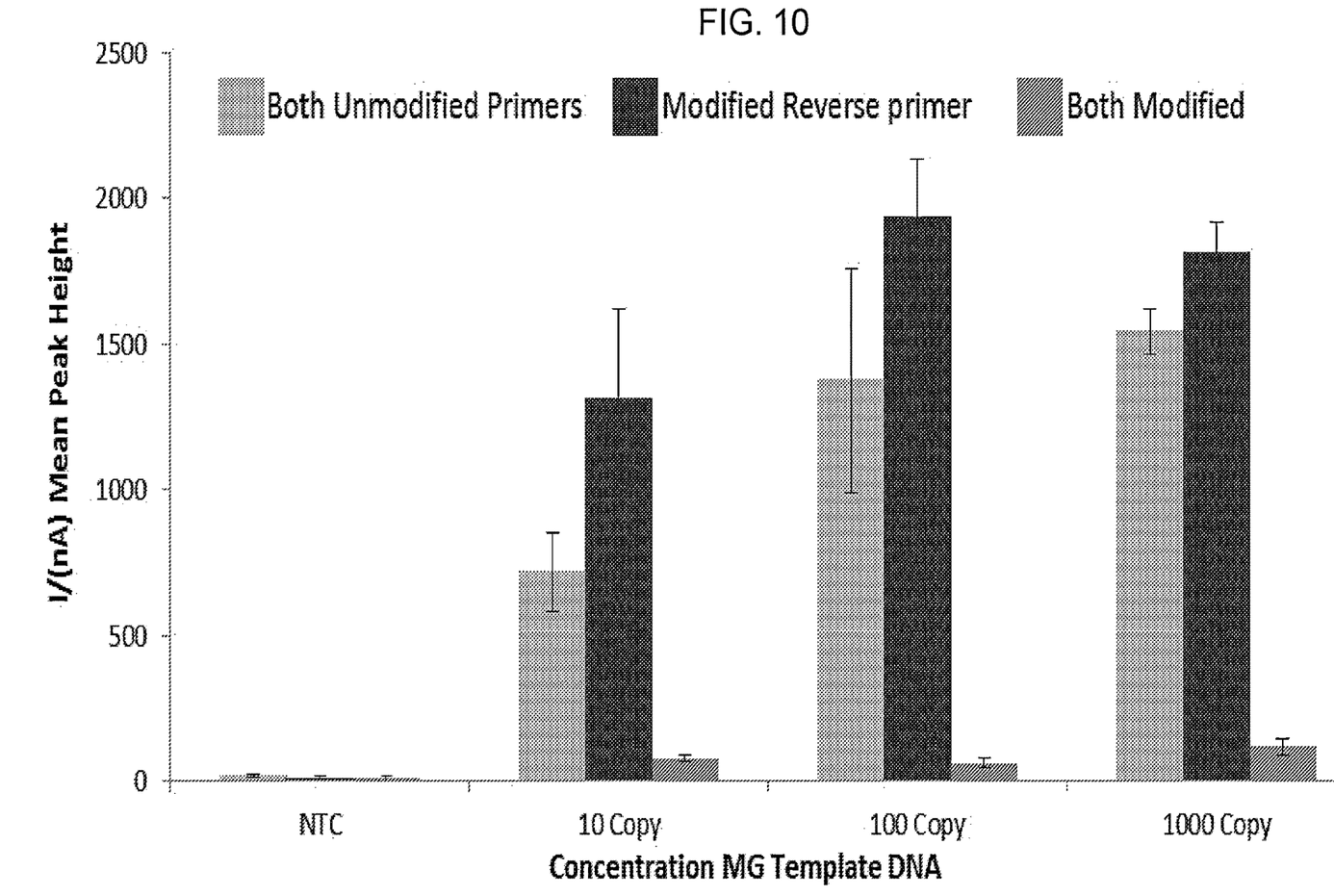
FIG. 10. Amplification and detection of *Mycoplasma genitalium* target sequence using standard and 4-base modified forward and reverse primers using semi-rapid PCR.

An experiment was carried out that amplified a serial dilution of a *C. trachomatis* template with a consistent amount of internal control using standard unmodified reverse primers and 4-base modified reverse primers. The two amplified nucleic acids were detected electrochemically. Results of these experiments are provided in FIG. 7. FIG. 7 shows that the internal control is capable of being consistently amplified and detected using an assay involving standard unmodified Rv primer or modified Rv primer in the presence of a range of *C. trachomatis* templates. Therefore, using a *C. trachomatis* Rv primer with 4 phosphorothioate nucleosides at the 5'end does not affect the amplification or detection of the internal control across a range of *C. trachomatis* template concentration s Compatibility of the Modified Rv with the Integrated Cartridge Cartridges were produced in which standard unmodified Rv primers (ABR114) or 4-base modified Rv primers (ABR115) were used to allow the performance of the different primers to be assessed on integrated cartridges. Ten replicates of each of 500 IFU and 0 IFU samples per cartridge type were amplified on the cartridge and detected in the cartridge using a cartridge reader. The results of these experiments are shown in FIG. 8 below. FIG. 8 shows that using the modified *C. trachomatis* Rv primer increased the mean peak height by ~2.2 fold in the outer chamber of the cartridge and by ~1.6 fold for the inner chamber of the cartridge for *C. trachomatis* positive samples compared to using standard unmodified primers. The 0 IFU samples were unaffected by the modified primer thereby increasing the signal-noise ratio.

Comparison of Standard Primers and Modified Primers in *N. gonhorroeae* Assay

In order to determine the different effects of using different combinations of modified and unmodified primers, experiments were performed in which 1000 copies of *N. gonhorroeae* were amplified and detected electrochemically. The results of these experiments are shown in FIG. 9.

In the *N. gonhorroeae* assay, the probe hybridises to the strand extended from the forward primer. Therefore, the forward primer, rather than the reverse primer is modified to prevent degradation, i.e. the first primer is the forward primer and the second primer is the reverse primer. Where both forward and reverse primers are modified to include 4 phosphorothioate nucleosides, both strands are protected from degradation by the exonuclease. This prevents the probe from hybridising to the amplified target nucleic acid, resulting in a large signal decrease.

Modifying the reverse primer rather than the forward primer means that the strand to which the probe binds is not protected from exonuclease degradation but the other strand is protected from degradation. Therefore, the majority of copies of the strand to which the probe binds will be degraded by exonuclease preventing hybridisation of the probe.

Using unmodified forward and reverse primers provides a control level of amplification in the presence of the *N. gonhorroeae* target sequence.

Modifying the forward primer, but not the reverse primer at the 5'end provides protection from exonuclease degradation for the first strand to which the probe binds, meaning that only the other strand is degraded. Probe is able to bind to the first strand, and the probe is degraded to provide a signal. Degradation of the probe allows further probe molecules to bind to the first strand and provide an increased signal. This causes a substantial increase in the mean peak height compared to the peak height when using unmodified primers.

Comparison of Standard Primers and Modified Primers in Assay for Internal Control In order to determine the different effects of using different combinations of modified and unmodified primers, experiments were performed in which 100 pg of internal control nucleic acid was amplified and detected electrochemically. The results of these experiments are shown in FIG. 10.

In the internal control amplification reaction, the probe hybridises to the strand extended from the reverse primer. Therefore, the reverse primer, rather than the forward primer is modified to prevent degradation, i.e. the first primer is the reverse primer and the second primer is the forward primer. Where both forward and reverse primers are modified to include 4 phosphorothioate nucleosides, both strands are protected from degradation by the exonuclease. This prevents the probe from hybridising to the amplified target nucleic acid, resulting in a large signal decrease.

Modifying the forward primer rather than the reverse primer means that the strand to which the probe binds is not protected from exonuclease degradation but the other strand is protected from exonuclease degradation but the other strand is protected from degradation. Therefore, the majority of copies of the strand to which the probe binds will be degraded by exonuclease preventing hybridisation of the probe.

Using unmodified forward and reverse primers provides a control level of amplification in the presence of internal control nucleic acid.

Modifying the reverse primer, but not the forward primer at the 5'end provides protection from exonuclease degradation for the first strand to which the probe binds, meaning that only the other strand is degraded. Probe is able to bind to the first strand, and the probe is degraded to provide a signal. Degradation of the probe allows further probe molecules to bind to the first strand and provide an increased signal. This causes a substantial increase in the mean peak height compared to the peak height when using unmodified primers.

Comparison of Standard Primers and Modified Primers in *M. genitalium* Assay

In order to determine the different effects of using different combinations of modified and unmodified primers, experiments were performed in which varying copy numbers of *M. genitalium* were amplified and detected electrochemically. The results of these experiments are shown in FIG. 11.

In the *M. genitalium* assay, the probe hybridises to the strand extended from the reverse primer. Therefore, the reverse primer, rather than the forward primer is modified to prevent degradation, i.e. the first primer is the reverse primer and the second primer is the forward primer. Where both forward and reverse primers are modified to include 4 phosphorothioate nucleosides, both strands are protected from degradation by the exonuclease. This prevents the probe from hybridising to the amplified target nucleic acid, resulting in a large signal decrease.

Using unmodified forward and reverse primers provides a control level of amplification in the presence of *M. genitalium* target sequence.

Modifying the reverse primer, but not the forward primer at the 5'end provides protection from exonuclease degradation for the strand to which the probe binds, meaning that only the other strand is degraded. Probe is able to bind to the first strand, and the probe is degraded to provide a signal. Degradation of the probe allows further probe molecules to bind to the first strand and provide an increased signal. This causes a substantial increase in the mean peak height compared to the peak height when using unmodified primers.

REFERENCES

1 Wiedmann M. et al. PCR Methods and Applications 1994 3(4)S51-64
2 Walker et al. Nucleic Acids Res. 1992. 20(7) 1691-1696
3 Wroblewski J. et al. J. Clin. Microbiol. 2006:44(9):3306-3312
4 Compton J. Nature 1991:350(6313):91-2
5 Vincent M. et al. EMBO Rep. 2004 5(8) 795-800
6 Notomi et al. Res. 2000 23 (12):E63.

The invention claimed is:

1. A nucleic acid amplification method comprising:
amplifying a sample, with a first primer comprising at least one modified nucleotide and a second primer to provide a double stranded nucleic acid comprising a first strand comprising the first primer and a downstream amplified region and a second strand, wherein the first primer comprises SEQ ID NO: 1 or 2;
incubating the double stranded nucleic acid with a 5' to 3' first exonuclease that hydrolyzes the second strand but not the first strand;
hybridizing a probe comprising a label to the first strand;
hydrolyzing the probe with a second exonuclease that does not hydrolyze the first strand, to produce a detectable signal from the label; and
repeating hybridization and hydrolysis of the probe to provide an increase in the detectable signal.

2. The method of claim 1, further comprising incubating the sample with uracil-N-glycosylase to hydrolyze nucleic acid containing uracil; and performing the amplifying step with dUTP in the absence of dTTP.

3. The method of claim 1, wherein amplifying the sample is achieved using PCR.

4. The method of claim 1, wherein the at least one modified nucleotide comprises at least one modified nucleobase, at least one modified sugar moiety, at least one phosphorothioate linkage, or at least one phosphoramidite linkage.

5. The method of claim 4, wherein the at least one modified nucleotide comprises at least one modified sugar moiety.

6. The method of claim 4, wherein the at least one modified nucleotide comprises a phosphorothioate linkage.

7. The method of claim 4, wherein the at least one modified nucleotide comprises a phosphoramidite linkage.

8. The method of claim 1, wherein the first primer comprises at least 4 modified nucleotides.

9. The method of claim 1, wherein the first and/or second exonuclease is T7 exonuclease.

10. The method of claim 1, wherein the label is an electrochemical label.

11. The method of claim 10, wherein the electrochemical label is a ferrocene label.

12. The method of claim 1, wherein the second primer comprises the other of SEQ ID NOS: 1 or 2.

13. A method of detecting a genetic target, the method comprising:
annealing a primer comprising SEQ ID NO: 1 or 2 to nucleic acid in a sample, the primer comprising at least one modified nucleotide;
extending the primer to create a copy of the genetic target;
hybridizing a first labeled probe to the copy; and
digesting the first labeled probe with an exonuclease to release a label from the probe and generate a detectable signal while the at least one modified nucleotide prevents the exonuclease from digesting the copy.

14. The method of claim 13, further comprising annealing a second labeled probe to the copy and digesting the second labeled probe to increase a signal-to-noise ratio of the detectable signal.

15. The method of claim 13, wherein the at least one modified nucleotide comprises at least one modified nucleobase, at least one modified sugar moiety, at least one phosphorothioate linkage, or at least one phosphoramidite linkage.

16. The method of claim 13, wherein the exonuclease is T7 exonuclease.

17. The method of claim 13, wherein the label is an electrochemical label.

18. The method of claim 17, wherein the electrochemical label is a ferrocene label.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
agattccaga ggcaatgcca aagaaa                                    26

<210> SEQ ID NO 2
<211> LENGTH: 29
<212> TYPE: DNA
<213> ORGANISM: Artificial Sequence
<220> FEATURE:
<223> OTHER INFORMATION: Synthetic

<400> SEQUENCE: 2
gtttggacac tagtcagcat caagctagg                                 29